United States Patent [19]

Huan

[11] Patent Number: 5,347,996
[45] Date of Patent: Sep. 20, 1994

[54] MOUTH OPENER

[76] Inventor: Lee C. Huan, Fl. 12, No. 25, Lane 175, Sec. 1, Kienkwo S. Rd., Taipei, Taiwan

[21] Appl. No.: 992,022

[22] Filed: Dec. 17, 1992

[51] Int. Cl.$^5$ .............................................. A61B 1/24
[52] U.S. Cl. ...................................... 128/12; 128/859; 433/140; 433/149
[58] Field of Search ................................... 128/12–15, 128/859, 861, 16, 848, 860, 862; 433/6, 140, 149; 119/821

[56] References Cited

U.S. PATENT DOCUMENTS

| 278,259 | 5/1883 | Nevius | 128/12 |
| 854,898 | 5/1907 | Lorenz | 128/12 |
| 856,352 | 6/1907 | Magoon | 128/12 |
| 892,682 | 7/1908 | Price | 128/12 |
| 2,220,674 | 11/1940 | Bloomheart | 128/12 |
| 2,614,325 | 10/1952 | Hartig | 128/12 |
| 3,217,708 | 11/1965 | Roberts | 128/12 |
| 3,518,988 | 7/1970 | Gores | 128/861 |
| 4,690,640 | 9/1987 | Hinz | 433/6 |
| 5,152,301 | 10/1992 | Kittelsen et al. | 128/861 |

FOREIGN PATENT DOCUMENTS 13706 of 1907 United Kingdom .................. 128/13

Primary Examiner—Richard J. Apley
Assistant Examiner—Donna L. Maraglio
Attorney, Agent, or Firm—Morton J. Rosenberg; David I. Klein

[57] ABSTRACT

This invention relates to a mouth opener with the configuration of integrated twin cups that can be divided into two parts, i.e. a linear configuration body and twin cup body. The two parts have the functions of structural framework and flexible mouth opening support. The head handle is the middle point, joining two tail troughs to form an angle that can produce physical resiliency, so the tail troughs will have flexible supporting function for the mouth. The two tail troughs are provided with bevels which are inserted between the user's upper and lower teeth to insure that the mouth opener is properly and securely positioned in the oral cavity. The belly support wall is a sturdy structure for reinforcement of the fixing and support functions. The remaining fine parts are also designed for the enforcement of aforementioned functions.

1 Claim, 4 Drawing Sheets

MOUTH OPENER

BACKGROUND OF THE INVENTION

It has been found that the conventional mouth opener on the market is too complicated in structure and difficult to operate. Hence, it is desired to have a mouth opener which is simple in construction and easy to use. Further, there is a need for a disposable mouth opener so as to prevent contagion.

Therefore, it is an object of the present invention to provide an improved mouth opener which may obviate and mitigate the above-mentioned drawbacks.

SUMMARY OF THE INVENTION

This invention relates to an improved mouth opener.

It is the primary object of the present invention to provide a mouth opener which is easy to operate.

It is another object of the present invention to provide a mouth opener which is simple in construction.

It is still another object of the present invention to provide a mouth opener which may be disposed of after use.

It is still another object of the present invention to provide a mouth opener which is facile to fabricate.

It is a further object of the present invention to provide a mouth opener which is inexpensive in cost.

Other objects and merits and a fuller understanding of the present invention will be obtained by those having ordinary skill in the art when the following detailed description of the preferred embodiment is read in conjunction with the accompanying drawings.

DETAILED DESCRIPTION OF THE PREFERRED EMBODIMENT

Figure 1:
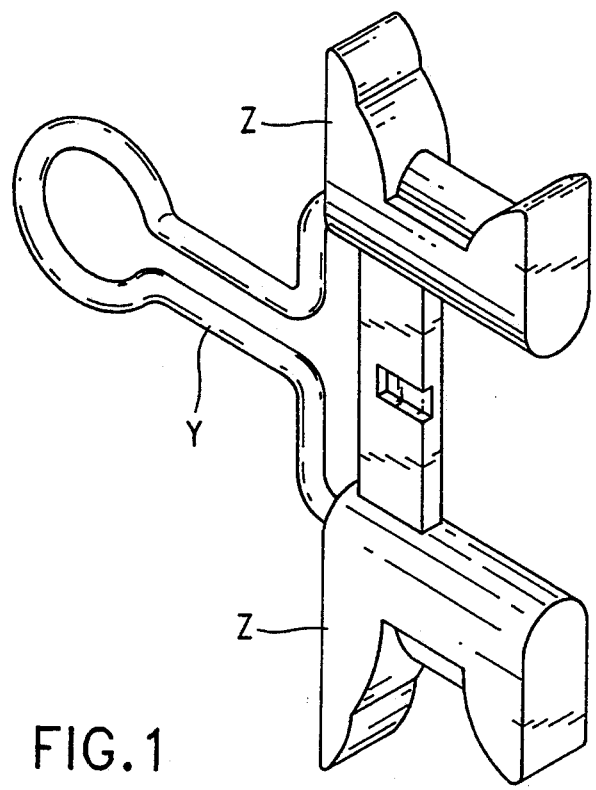
FIG. 1 is a perspective view of the present invention.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alternations and further modifications in the illustrated device, and such further applications of the principles of the invention as illustrated herein being contemplated as would normally occur to one skilled in the art to which the invention relates.

Figure 2:
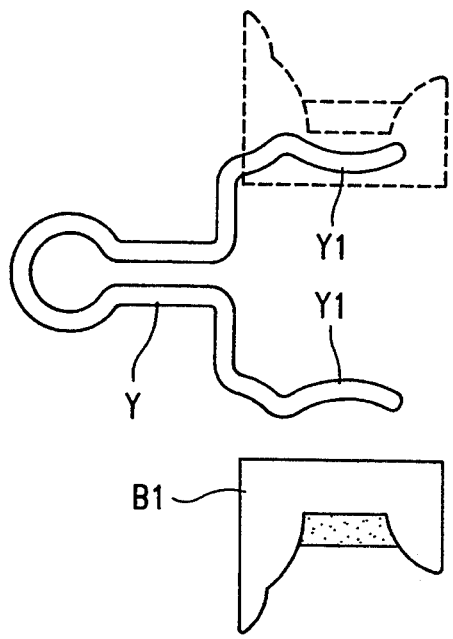
FIG. 2 is an exploded view of the present invention.
Figure 2A:
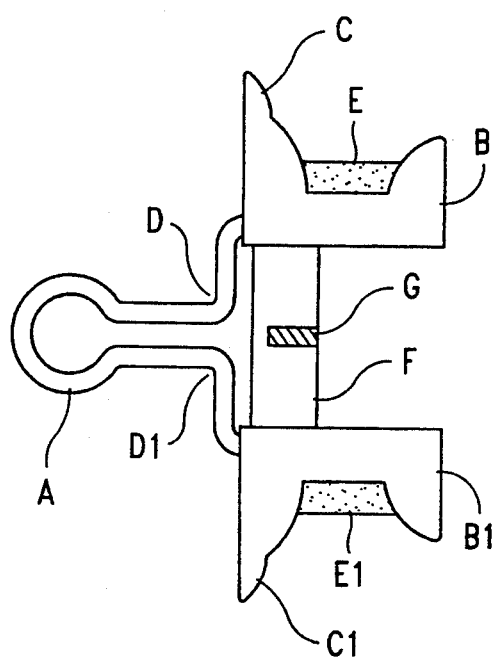
FIG. 2A is a front view of the present invention.
Figure 3:
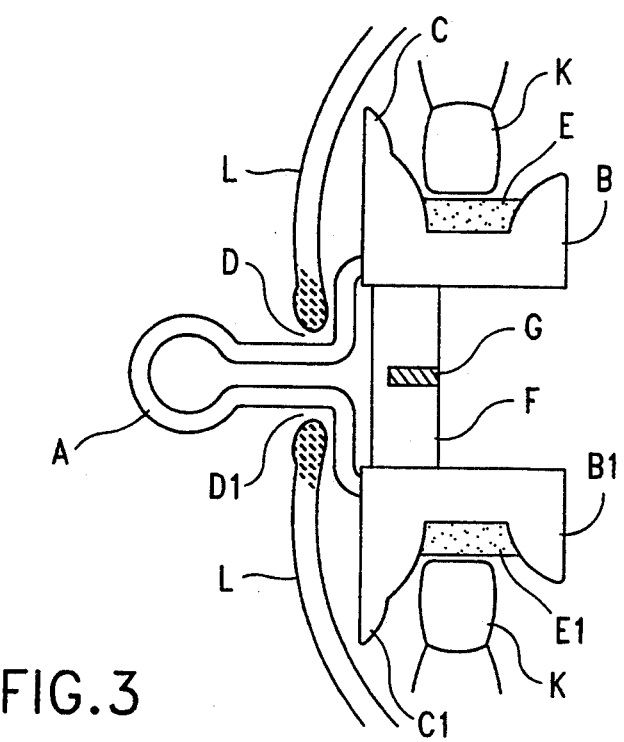
FIG. 3 is a working view of the present invention.
Figure 4:
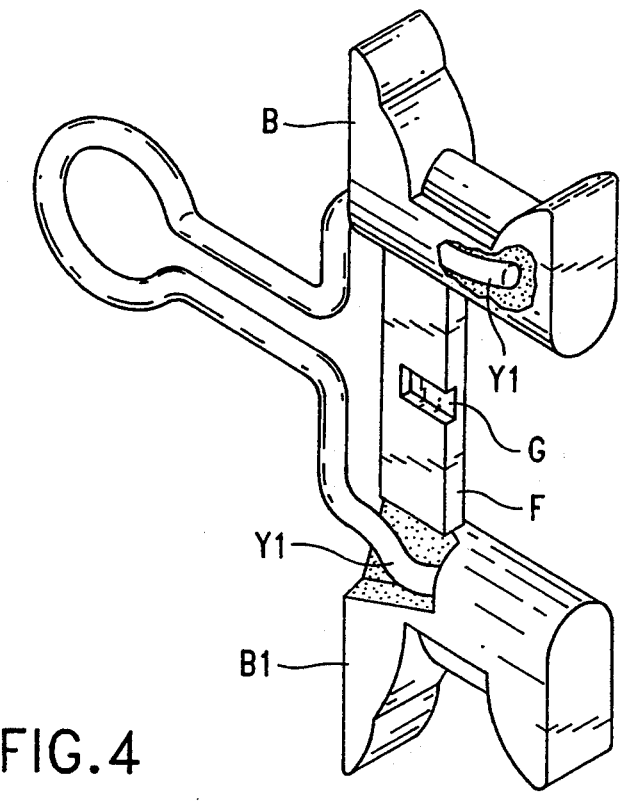
FIG. 4 is a perspective view showing the interior structure of the jaw.
Figure 5:
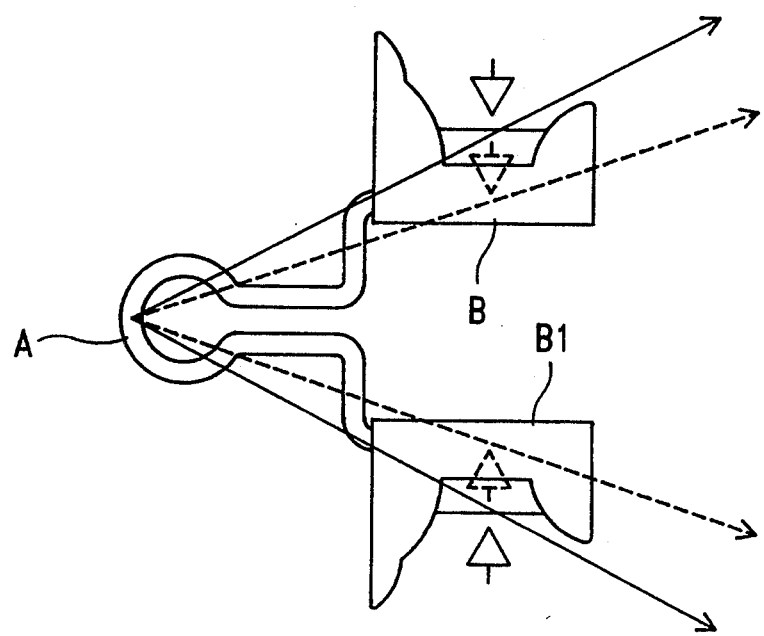
FIG. 5 is a perspective view of the mouth opener of the present invention showing the resiliency of the mouth opener when it is compressed by forces exerted by the user's teeth.
Figure 6:
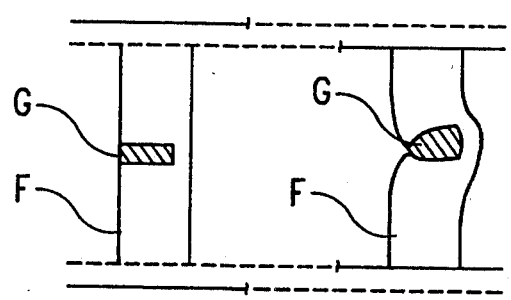
FIG. 6 is a perspective view of the belly support wall of the mouth opener of the present invention showing the resiliency imparted to the belly support wall by the recess therein.
Figure 7:
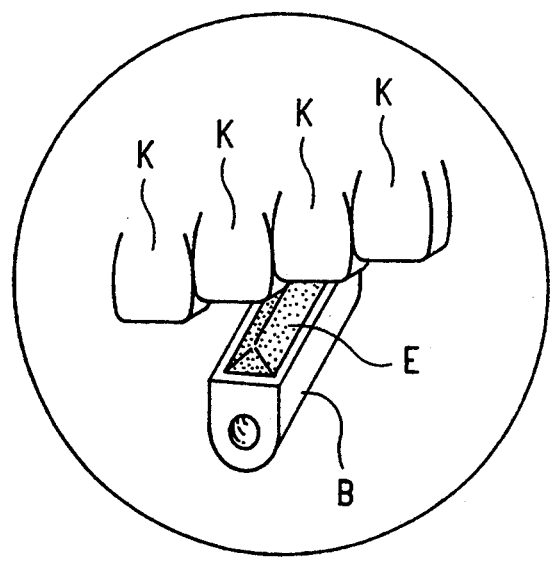
FIG. 7 is an enlarged view of the upper tail trough and its associated bevel of the mouth opener of the present invention as they are engaged by the upper teeth of the user; and, FIG. 8 is an enlarged cross-sectional view of the tail trough of the mouth opener of the present invention.
Figure 8:
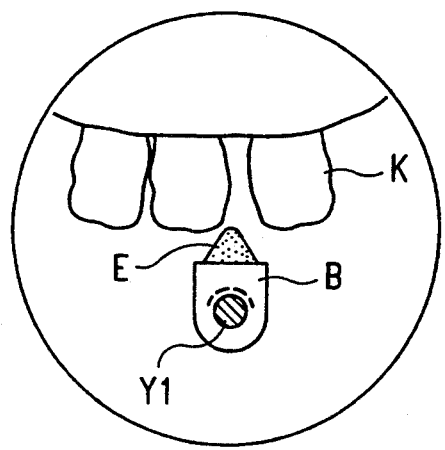

With reference to the drawings and in particular to FIGS. 1, 2 and 2A thereof, the mouth opener according to the present invention mainly comprises a substantially Y-shaped body or frame member Y and a twin cup body Z. The Y-shaped body Y is provided with a head handle A and two necks D and D1, while the twin cup body Z has two spaced apart tail troughs or U-shaped members B and B1, two shoulders C and C1, and two bevels E and E1. Further, a belly support wall F with a central recess G is mounted at the intermediate portion of the twin cup body Z. As illustrated, the head handle A associated with the tail troughs B and B1 forms an angle that can produce physical resiliency (see FIG. 5) so that the tail troughs B and B1 will have flexible supporting function between the lower and upper teeth K in the mouth (see FIG. 3) the tail troughs B and B1 being movable relative to each other. The recess of the tail troughs B and B1 is engaged with the clearance between two teeth thereby keeping the the mouth opener in place (see FIGS. 3 and 7). The shoulders C and C1 are disposed between the lips L and the teeth K for providing assistance for the steadiness of the mouth opener. The necks D and D1 are also designed to provide assistance for the steadiness of the mouth opener and to provide the lips with a larger activity space. The tail troughs B and B1 are respectively provided with bevels E and E1 which are inserted between teeth K for ensuring steadiness and fixing of the mouth opener (see FIG. 7). The twin cup body Z has a belly support wall F which is used to reinforce the fixing and support functions. The recess G is compressible and is associated with the resiliency of the material of the jaws Z and the main body Y to reduce the impact of the tail troughs B and B1 on the teeth K when the mouth opener is disposed into the mouth. The Y-shaped body Y is provided with spaced apart concave legs Y1 (see FIG. 4) which acts as a skeleton for strengthening the engagement between the mouth opener and the teeth K.

Although the present invention has been described with a certain degree of particularity, it is understood that the present disclosure is made by way of example only and that numerous changes in the detail of construction and the combination and arrangement of parts may be resorted to without departing from the spirit and scope of the invention as hereinafter claimed.

I claim:

1. A mouth opener comprising:
    a planar substantially Y-shaped frame member having a handle and two spaced apart legs extending from said handle;
    a twin cup body having a pair of spaced apart U-shaped members affixed on respective legs of, and lying in substantially the same plane as, said substantially Y-shaped frame member, wherein said handle and said U-shaped members generally form an angle which allows said U-shaped members to be moved relative to each other, each of said U-shaped members having a proximal shoulder adapted to fit between a lip and a row of teeth of a user of said mouth opener for steadying said mouth opener in the oral cavity of the user;
    a bevel disposed in each of said U-shaped members for inserting between adjacent teeth to insure steadiness and fixation of said mouth opener in the oral cavity of the user; and,
    a resilient support wall extending between and connected to said U-shaped members, said support wall having a recess formed therein for allowing said support wall to be compressed so that said U-shaped members move with respect to each other.

* * * * *